(12) United States Patent
Broadbent et al.

(10) Patent No.: US 8,667,844 B1
(45) Date of Patent: Mar. 11, 2014

(54) ULTRASONIC SCALAR ADHESION TEST APPARATUS AND METHOD FOR PAINTS AND FINISHES

(75) Inventors: Christopher L. Broadbent, Kent, WA (US); Michael P. Murphy, Bellingham, WA (US); Randall Jahren, Bainbridge Island, WA (US)

(73) Assignee: The Boeing Company, Chicago, IL (US)

(*) Notice: Subject to any disclaimer, the term of this patent is extended or adjusted under 35 U.S.C. 154(b) by 409 days.

(21) Appl. No.: 13/016,905

(22) Filed: Jan. 28, 2011

(51) Int. Cl.
*G01M 7/00* (2006.01)

(52) U.S. Cl.
USPC ................ 73/588; 73/775; 73/827; 73/150 A

(58) Field of Classification Search
USPC ................ 73/582, 588, 775, 827, 150 A, 649
See application file for complete search history.

(56) References Cited

U.S. PATENT DOCUMENTS

| | | | | | |
|---|---|---|---|---|---|
| 3,770,593 | A | * | 11/1973 | Dick | 205/776.5 |
| 3,890,831 | A | * | 6/1975 | Cusick et al. | 73/588 |
| 4,393,699 | A | * | 7/1983 | Seiler, Jr. | 73/150 A |
| 4,413,510 | A | * | 11/1983 | McCusker et al. | 73/150 A |
| 4,606,225 | A | * | 8/1986 | Thomason et al. | 73/150 A |
| 4,819,489 | A | * | 4/1989 | Nelson et al. | 73/854 |
| 4,843,874 | A | * | 7/1989 | Tsuyoshi et al. | 73/150 R |
| 4,856,326 | A | * | 8/1989 | Tsukamoto | 73/150 A |
| 5,027,650 | A | * | 7/1991 | Oblas et al. | 73/150 A |
| 5,325,713 | A | * | 7/1994 | Furst et al. | 73/150 R |
| 5,412,997 | A | * | 5/1995 | Hu et al. | 73/827 |
| 5,454,260 | A | * | 10/1995 | Wang | 73/150 A |
| 5,460,859 | A | * | 10/1995 | Reale | 427/560 |
| 6,220,099 | B1 | * | 4/2001 | Marti et al. | 73/633 |
| 6,490,047 | B2 | * | 12/2002 | Siu | 356/502 |
| 6,538,725 | B2 | * | 3/2003 | Potyrailo et al. | 356/32 |
| 6,604,420 | B2 | * | 8/2003 | Hawbaker et al. | 73/588 |
| 6,711,938 | B2 | * | 3/2004 | Huff | 73/37 |
| 6,813,951 | B2 | * | 11/2004 | Blouin et al. | 73/643 |
| 6,981,408 | B1 | * | 1/2006 | Madanshetty | 73/150 A |
| 7,123,725 | B2 | * | 10/2006 | Boesch et al. | 381/58 |
| 7,220,966 | B2 | * | 5/2007 | Saito et al. | 250/341.6 |
| 7,263,777 | B2 | * | 9/2007 | Adams | 33/32.6 |
| 7,286,241 | B2 | * | 10/2007 | Drake, Jr. | 356/502 |

(Continued)

OTHER PUBLICATIONS

Data Sheet for Elcometer 106 Pull Off Adhesion Tester, http://www.elcometer.com/images/stories/PDFs/Datasheets/English/106.pdf (current version published Jan. 10, 2004; date of first publication unknown).

(Continued)

*Primary Examiner* — Peter Macchiarolo
*Assistant Examiner* — Samir M Shah
(74) *Attorney, Agent, or Firm* — Melissa Glauber

(57) ABSTRACT

Presented is a system and method for testing the adhesion of coatings to substrates using an ultrasonic scalar. The system comprises a body, a flexible scalpel extending from said body, and a source of ultrasonic waves. The flexible scalpel applies pressure and ultrasonic waves to a coating that is removed when the adhesion of the coating to the substrate is substandard. The method comprises applying an flexible scalpel extending from an ultrasonic adhesion test device to a coating, applying ultrasonic waves through the flexible scalpel to the coating while moving across the coating, removing the coating if there is less than an acceptable adhesion of the coating to the substrate, and inspecting the coating to determine if coating was removed from the substrate.

20 Claims, 4 Drawing Sheets

(56) References Cited

U.S. PATENT DOCUMENTS

| | | | |
|---|---|---|---|
| 7,640,809 B2* | 1/2010 | Shibata et al. | 73/622 |
| 7,770,454 B2* | 8/2010 | Sokol et al. | 73/588 |
| 8,226,894 B2* | 7/2012 | Miyake et al. | 422/128 |
| 8,231,644 B2* | 7/2012 | Onaga | 606/169 |
| 8,322,207 B2* | 12/2012 | Chew et al. | 73/150 A |
| 8,347,723 B2* | 1/2013 | Questo et al. | 73/588 |
| 2009/0030325 A1* | 1/2009 | Hyuga | 600/459 |
| 2009/0031812 A1* | 2/2009 | Shibata et al. | 73/622 |
| 2009/0224443 A1* | 9/2009 | Rundquist et al. | 266/99 |
| 2009/0241656 A1* | 10/2009 | Jacquemin | 73/150 A |
| 2010/0071456 A1* | 3/2010 | Chew et al. | 73/150 A |
| 2010/0206062 A1* | 8/2010 | Yoon et al. | 73/150 A |
| 2011/0138926 A1* | 6/2011 | Bassot et al. | 73/826 |
| 2011/0188251 A1* | 8/2011 | Kalms et al. | 362/259 |
| 2011/0283767 A1* | 11/2011 | Questo et al. | 73/1.82 |

OTHER PUBLICATIONS

Data Sheet for Elcometer 109 Tensile Adhesion Tester, http://www.elcometer.com/images/storiesPDFs/Datasheets/English/109.pdf (current version published Mar. 5, 2006; date of first publication unknown).

Web page featuring JorVet Piezoelectric Ultrasonic Scaler, http://www.jorvet.com/catalog/product_info.php/products_id/4506?osCsid=643a6153113d70628546ebd59ff2b4a0 (current version published Nov. 22, 2006; date of first publication unknown).

Data Sheet for PosiTest Pull-Off Adhesion Tester, http://www.defeisko.com/adhesion-tester/PosiTestAT.pdf (current version published 2009; date of first publication unknown).

ASTM Standard D3330 / D330M, 2010, "Standard Test Method for Peel Adhesion of Pressure-Sensitive Tape," ASTM International, West Conshohocken, PA, www.astm.org.

* cited by examiner

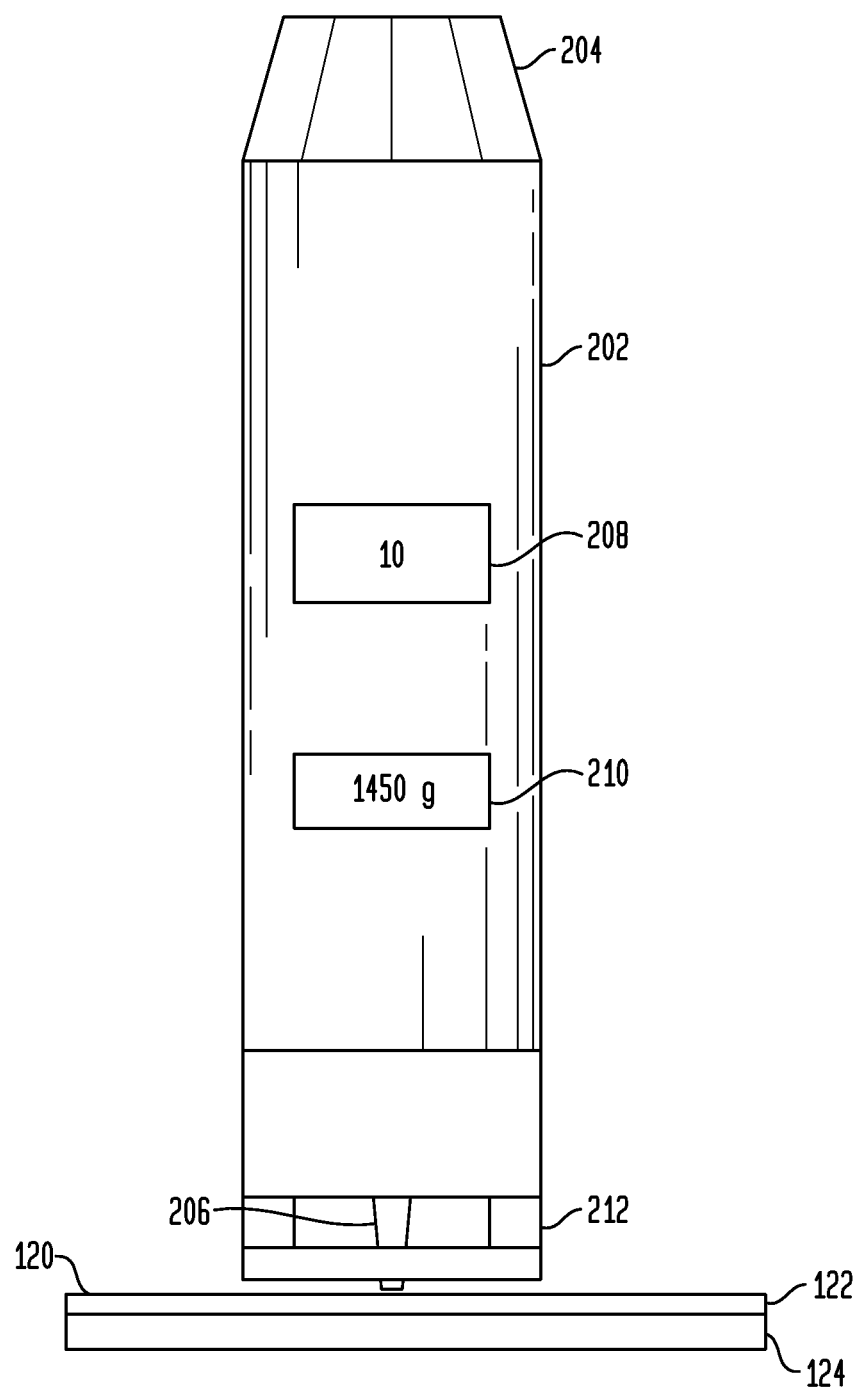

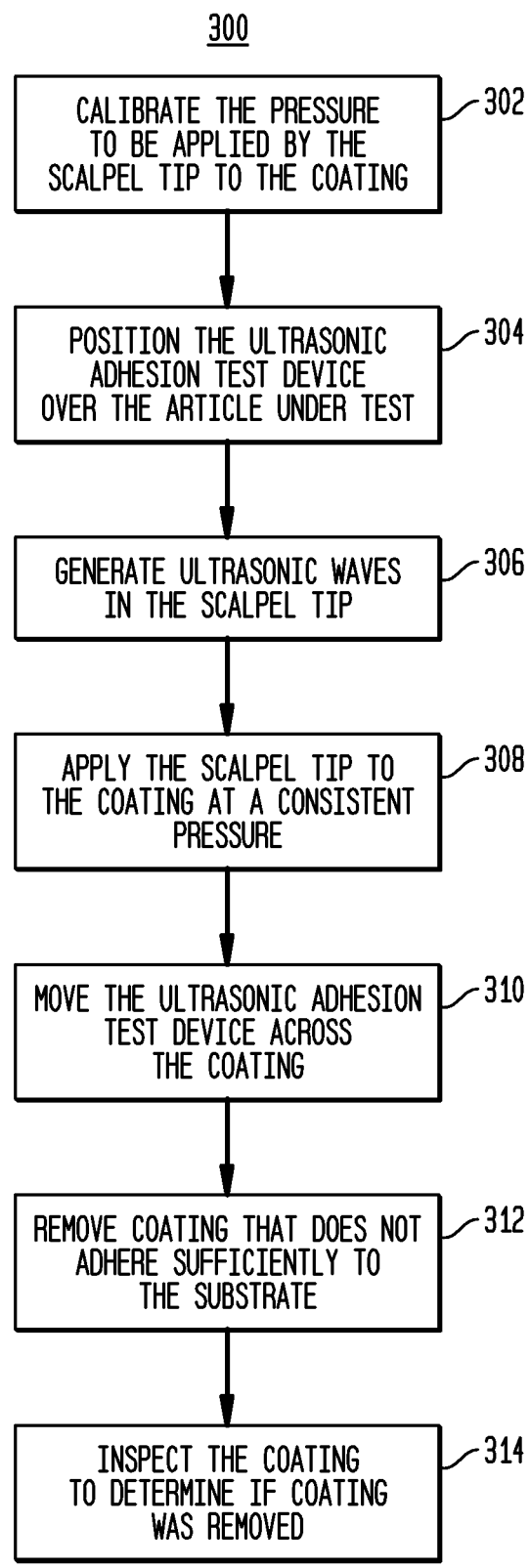

ULTRASONIC SCALAR ADHESION TEST APPARATUS AND METHOD FOR PAINTS AND FINISHES

FIELD

Embodiments of the subject matter described herein relate generally to a system and method for testing the adhesion of paints and finishes using an ultrasonic scalar.

BACKGROUND

Many articles, such as parts or finished goods, have paints or finishes applied to them as part of their manufacturing process. How well a paint or finish adheres to the surface of an article to which it is applied depends upon several factors, including: the paint or finish composition, the surface composition, the conditioning of the surface prior to application of paint or finish, the presence of an undercoat or intercoat prior to application of an outer coat, the temperature and humidity during application, the method of curing or drying of the paint or finish, and the time allowed for the paint or finish to cure or dry. However, even with rigidly controlled manufacturing processes, variations in paint and finish adhesion occur.

To determine the adhesion to the article surface, organic coatings are sometimes tested using a material or device that is pressed against the coating surface for a certain duration and then removed. For example, a material such as a pressure sensitive adhesive tape is secured to the coating and then removed. If any coating is removed with the tape, then the adhesion of the coating is deemed to have failed the test. There are several variations of these adhesion tests, including rollers that press the tape to the coating at a predetermined pressure, water saturated materials that pre-soak the coating prior to application of the tape, and scribes that physically score the coating prior to application of the tape. The water and scoring facilitate the tape's ability to remove coating from the underlying surface and make it easier to assess if the coating is adhering poorly.

In another example, a metal dolly having a flat circular surface is secured to the coating using an adhesive. Once the adhesive has cured, the dolly is pulled at various pressures until the dolly pulls the coating from the article or the adhesive detaches from the dolly or coating. In one variation of this method, a cutting tool is used to drill a channel through the coating to the article's surface around the dolly to isolate the test area. These test methods are destructive to the coating. Further, the test methods can damage the article under test if any scoring or drilling penetrates below the depth of the coating into the article itself. Therefore, these tests are typically performed on sample articles rather than on the actual goods to be sold. For example, a sample article from a batch of identically manufactured articles is selected at random from the batch to be the representative article and destructively tested using the methods described above. The assumption is that each article from the batch will have nearly identical coatings to the representative article because they were manufactured at approximately the same time under similar conditions.

There are several disadvantages to destructive test methods. First, if the articles under test are large or expensive items, such as aircraft bodies, it may be impractical to use destructive test methods. Second, even if the articles are manufactured under identical conditions, there may be differences in coating adhesion from article to article. Third, a false negative during testing of the representative article can result in disqualification of perfectly good articles in the batch, or at a minimum require further destructive testing of additional articles. Fourth, destructive testing of representative articles adds to overall costs. Fifth, because only representative articles are tested, not every article that is manufactured can be tested before being sold or used. The present test methods do not address these disadvantages. Therefore, there is a need to develop a non-destructive test method for testing the adhesion of coatings to articles.

SUMMARY

Presented is an ultrasonic adhesion test apparatus and method for non-destructive testing of coatings on articles. The ultrasonic adhesion test apparatus is only destructive when the coating fails to meet the desired adhesion strength. If the article meets the desired adhesion strength, the test is non-destructive. This test method and apparatus allows a tested good to be sold if the coating passes the test. The ultrasonic adhesion test apparatus and method also facilitates testing of large or expensive articles where destructive testing is cost prohibitive or impractical, ameliorates the effect of false negatives by allowing non-destructive testing of additional articles from a batch, eliminates the need for destructive testing of articles therefore reducing costs, and allows testing of the coatings on every article intended for sale or use, if needed or desirable.

In an embodiment, the ultrasonic adhesion test apparatus comprises a body, a flexible scalpel extending from the body, and a source of ultrasonic waves. The flexible scalpel receives the ultrasonic waves from the source, and applies the ultrasonic waves and a pressure to a coating. The ultrasonic waves and the pressure remove the coating from the substrate when the adhesion of the coating to the substrate is substandard.

In an embodiment, the system comprises a means for generating a plurality of ultrasonic waves in a scalar tip, a means for pressing the scalar tip onto a coating of a manufactured article at a consistent pressure and coupling the ultrasonic waves to the coating, a means for translating the scalar tip across the coating, and a means for cooling the scalar tip. The pressing of the scalar tip onto the coating, the translating of the scalar tip across the coating, and the coupling of the ultrasonic waves to the coating removes the coating from an underlying substrate when there is insufficient adhesion of the coating to the underlying substrate.

In an embodiment, the method for the ultrasonic adhesion test apparatus comprises applying an ultrasonic adhesion test device having a flexible scalpel that extends from the ultrasonic adhesion test device, to a coating, applying ultrasonic waves through the flexible scalpel to the coatings, moving the ultrasonic adhesion test device across the coating which removes coating when there is insufficient adhesion of the coating to the substrate, and inspecting the coating for insufficient adhesion of the coating to the substrate.

The features, functions, and advantages discussed can be achieved independently in various embodiments of the present disclosure or may be combined in yet other embodiments further details of which can be seen with reference to the following description and drawings.

BRIEF DESCRIPTION OF THE DRAWINGS

The accompanying figures depict various embodiments of the ultrasonic adhesion test apparatus and method. A brief description of each figure is provided below. Elements with the same reference number in each figure indicated identical or functionally similar elements. Additionally, the left-most digit(s) of a reference number indicate the drawing in which the reference number first appears.

FIG. 2a is a diagram of a portable adhesion test apparatus in one embodiment of the ultrasonic scalar adhesion test apparatus and method for paints and finishes;

FIG. 3 is a flowchart of operation of an adhesion test apparatus in one embodiment of the ultrasonic scalar adhesion test apparatus and method for paints and finishes.

DETAILED DESCRIPTION

The following detailed description is merely illustrative in nature and is not intended to limit the embodiments of the invention or the application and uses of such embodiments. Furthermore, there is no intention to be bound by any expressed or implied theory presented in the preceding technical field, background, brief summary or the following detailed description.

Prior art adhesion testers for coatings and finishes applied to manufactured articles typically cause damage to the coatings as part of the testing process. Some prior art adhesion testers can cause additional damage to the surface of the article when scribing is performed to the coating in order to isolate a portion of the coating under test from the surrounding coating. This generally renders the tested article unfit for use or sale after the testing.

Figure 1:
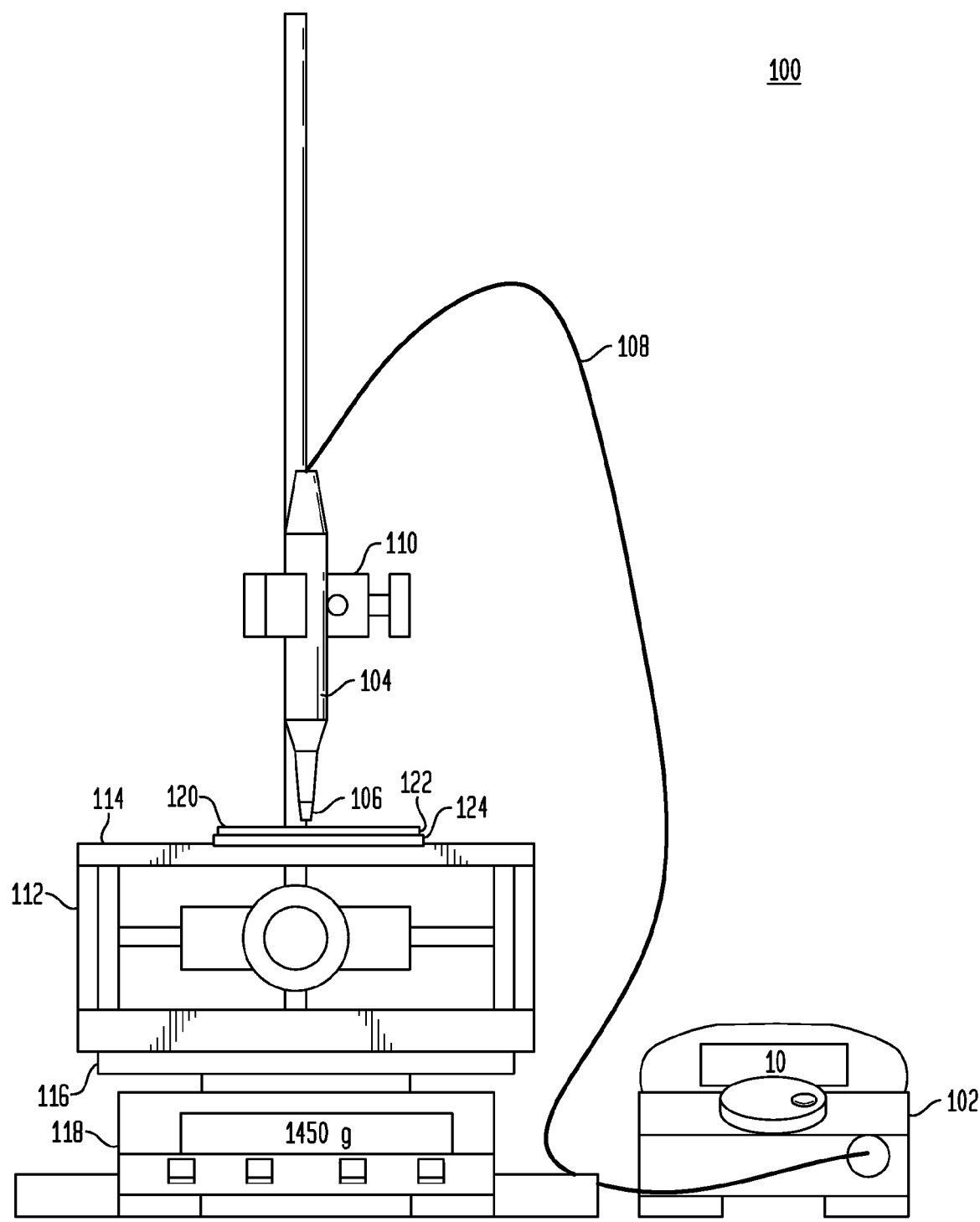
FIG. 1 is a diagram of an ultrasonic adhesion test apparatus in one embodiment of the ultrasonic scalar adhesion test apparatus and method for paints and finishes.

Referring now to FIG. 1, an ultrasonic adhesion test apparatus 100 is presented that performs non-destructive adhesion testing of coatings and finishes (collectively coatings 122) on surfaces, for example coatings 122 on manufactured articles. The ultrasonic adhesion test apparatus 100 comprises a power supply 102, a piezoelectric ultrasonic scalar 104 having a scalpel tip 106, sometimes called a scalar tip. In embodiments, the scalpel tip 106 is a point shape, a flat edged tip, or a flat edge tip with rounded corners. The scalpel tip 106 has a small cross section that contacts the coating 122, for example approximately 0.00058 square inches. The piezoelectric ultrasonic scalar 104 is attached to the power supply 102 via a line 108. The power supply 102 provides high frequency current, for example alternating current at 29 kHz, to the piezoelectric ultrasonic scalar 104 via the line 108. The high frequency current is applied to ceramic plates in the piezoelectric ultrasonic scalar 104 that generate ultrasonic waves at the scalpel tip 106. Water cools the scalpel tip 106 to keep the scalpel tip 106 from becoming hot due to the ultrasonic waves. An example piezoelectric ultrasonic scalar 104, scalpel tip 106, line 108 and power supply 102 is the JorVet Piezoelectric Ultrasonic Scalar used for dental work.

In operation, a mechanical positioning arm 110 holds the piezoelectric ultrasonic scalar 104 in place, while a translating scissoring platform 112 moves an article under test 120 under the scalpel tip 106. The translating scissoring platform 112 has a moveable top plate 114 connected to a base 116 that allows the moveable top plate 114 to be moved vertically and laterally (horizontally) relative to the base 116. The article under test 120 is secured to the moveable top plate 114 of the translating scissoring platform 112. The moveable top plate 114 is moved vertically until the article under test 120 is pressing against the scalpel tip 106 at a desired pressure, for example 1450 grams. A scale 118 placed under the base 116 of the translating scissoring platform 112 provides a measurement of the pressure. Pressures of between approximately 1100 grams and 1600 grams are contemplated, however pressures around or under 1100 grams may be insufficient to test the coating 122, while pressures around or above 1600 grams may remove coating 122 regardless of the adhesion of the coating 122 to the substrate 124.

Once the scalpel tip 106 of the piezoelectric ultrasonic scalar 104 is pressing against the article under test 120 at the desired pressure, the power supply 102 is energized and the piezoelectric ultrasonic scalar 104 begins to produce ultrasonic waves at the scalpel tip 106. The moveable top plate 114 is then translated, or moved laterally (horizontally) across a portion of the article under test 120, for example a one-inch portion of the article under test 120. The moveable top plate 114 is translated across the article under test 120 at a desired speed, for example 0.5 inches/sec, although speeds of less than 0.1 inches/sec to over 1 inch/sec are also contemplated.

The article under test 120 comprises one or more coatings 122 over a substrate 124. The scalpel tip 106 presses against the coatings 122 as the article under test 120 is translated under the piezoelectric ultrasonic scalar 104. Ultrasonic waves from the scalpel tip 106, in addition to the mechanical pressure applied by the scalpel tip 106, and the rate at which the scalpel tip 106 is translated across the article under 120 are controlled to test the adhesion of the coatings 122 to the underlying substrate 124. Because the scalpel tip 106 is cooled by water, there is little heat transferred to the coatings 122. The amount of energy provided to the piezoelectric ultrasonic scalar 104 by the power supply 102 is controlled and corresponds to the acceptable adhesion performance of the coatings 122 to the substrate 124. Power levels, pressures, and translation rates required for testing various coatings 122 and substrates 124 are predetermined, for example by testing samples at various power levels, pressures, and translations rates to determine when the coatings 122 fail to adhere to the substrates 124. These values become the set of parameters for performing the adhesion testing. Using the parameters for testing the adhesion of a particular coating 122 and substrate 124, the power levels and scalpel pressures of the ultrasonic adhesion test apparatus 100 are calibrated to the appropriate levels and the adhesion test is performed at a given translation rate. Example coatings 122 are top coats such as enamel and organic paints, and undercoats or intercoats such as primers. Example substrates 124 are steel, aluminum, carbon fiber or fiberglass composite, and thermoplastic.

The power levels and scalpel pressures of the ultrasonic adhesion test apparatus 100 can be calibrated so that only coatings 122 with substandard or insufficient adhesion to the substrate 124 are removed during testing. Generally, substandard or insufficient adhesion refers to adhesion of a coating 122 to a substrate 124 that fails to meet the applicable adhesion test. For example, if there is an industry standard then substandard or insufficient adhesion relates to coating 122 that fails to pass the test required to meet the standard. Alternatively, adhesion can also be substandard or insufficient if the adhesion is less than desirable for a particular application of the article to which the coating 122 is applied. In embodiments, the power levels and scalpel pressures of the ultrasonic adhesion test apparatus 100 can be calibrated to test the adhesion at any desired level of acceptable adhesion, for example testing for adhesions greater than required by a standard, or testing for adhesion at less than an application or standard requires. In embodiments, the results for various modulations of the power levels, pressures, and translation rates can be compared with results from prior art adhesion testing methods.

After scalpel tip 106 has translated across a portion of the article under test 120, the article under test is inspected, and may be further examined and evaluated using test equipment or test procedures. If the adhesion of the coatings 122 to the substrate 124 is substandard, the mechanical pressure and ultrasonic waves will loosen the coatings 122 and expose the substrate 124 indicating that the coating 122 has failed the adhesion test. However, the ultrasonic waves of the scalpel tip 106 will generally not damage or otherwise affect the substrate 124 or article under test 120 other than exposing the substrate 124. This allows the article under test 120 to be returned to the manufacturing facility to be reconditioned and later retested. If the ultrasonic waves did not loosen the coatings 122 and expose the substrate 124, then the adhesion of the coatings 122 to the substrate 124 meets the standard. Because the coatings 122 are still adhering to the substrate 124 and are therefore undamaged, the article under test 120 can be used or sold.

In embodiments, the adhesion test is a pass or fail test. If any coating 122 is removed then the coating 122 fails to meet the desired adhesion strength to the substrate 124 and the coating 122 fails the adhesion test, in this case destructively. If the coating 122 and substrate 124 meet the desired adhesion strength, then the coating 122 passes. Because the coating 122 remains attached to the substrate 124, the test is non-destructive for coatings 122 that pass the adhesion test.

Referring now to FIG. 2a, a portable adhesion test apparatus 200 is presented. The portable adhesion test apparatus 200 is similar in function to the ultrasonic adhesion test apparatus 100, however the components of the portable adhesion test apparatus 200 are packaged in a body 202 for portability. The body 202 allows a user to hold the portable adhesion test apparatus 200 during testing, and can be knurled or have a coating that assists the user in holding the portable adhesion test apparatus 200. In an embodiment, the portable adhesion test apparatus 200 comprises a body 202 that houses a power source, an electronic circuit for generating ultrasonic waveforms and driving the ultrasonic transducers such as such as piezoelectric ceramics (not shown) that produce ultrasonic waves. The ultrasonic transducers produce the ultrasonic waves that are coupled to the flexible scalpel tip 206. In addition to piezoelectric ceramics, any means of generating ultrasonic waves in the scalpel tip 106 as would be known in the art, as well as generating ultrasonic waves at different frequencies, is also contemplated.

The body 202 has a rotating dial 204 at the top of the body 202 that allows the power level to be changed. A display window 208 presents the current power level to the user. A second display window presents the current pressure of the flexible scalpel tip 206 against an article under test 120. The flexible scalpel tip 206 protrudes from the base of the body 206 through an adjustable mechanical guide 212 at the base of the body 202. The adjustable mechanical guide 212 is adjusted up and down prior to operation of the portable adhesion test apparatus 200 to expose more or less of the flexible scalpel tip 206 beyond the adjustable mechanical guide 212. By exposing more of the flexible scalpel tip 206, more pressure is exerted against the article under test 120 when the portable adhesion test apparatus 200 is positioned against an article under test 120. By exposing less of the flexible scalpel tip 206, less pressure is exerted against the article under test 120. Once the flexible scalpel tip 206 is calibrated to the proper pressure, the adjustable mechanical guide 212 is locked into place. The adjustable mechanical guide 212 acts as a stop, and allows the flexible scalpel tip 206 to produce a constant pressure against the coatings 122 of the articles under test 120. In operation, the adjustable mechanical guide 212 is pressed against the article under test 120. The adjustable mechanical guide 212 slides over the coating 122 while the flexible scalpel tip 206 bends under pressure against the coating 122 of the article under test 120. This arrangement of the flexible scalpel tip 206 and adjustable mechanical guide 212 allows the user to hold the portable adhesion test apparatus 200 at a greater and less precise pressure against the article under test 120 to maintain contact of the adjustable mechanical guide 212 against the article under test 120 during testing, while the flexible scalpel tip 206 maintains a controlled scalpel pressure against the coating 122.

Figure 2B:
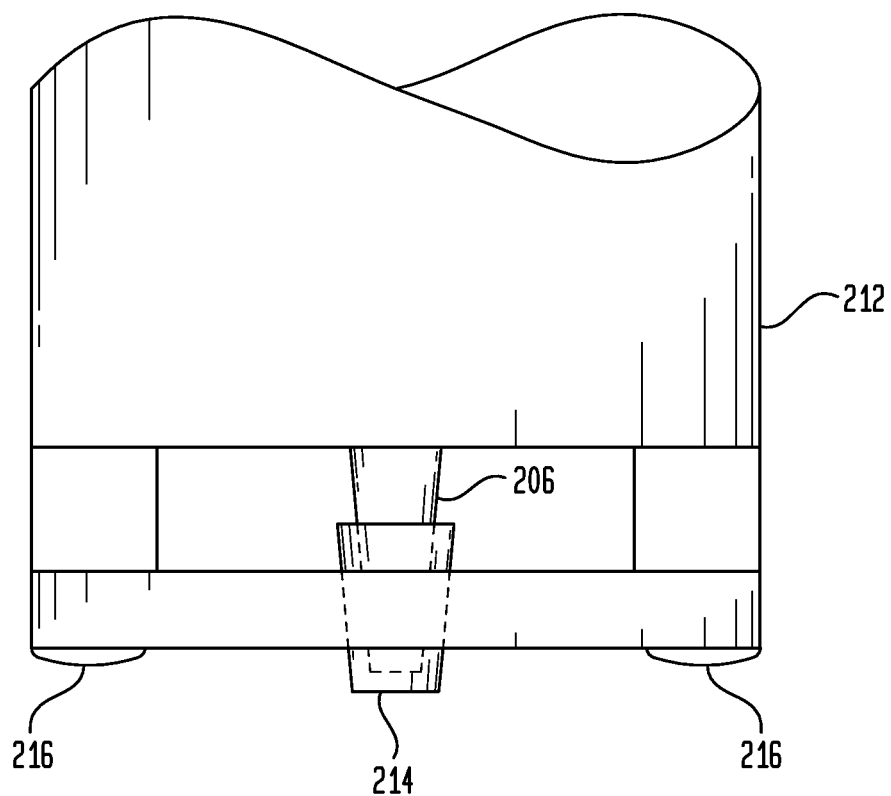
FIG. 2b is a diagram of anti-marring features of the portable adhesion test apparatus in one embodiment of the ultrasonic scalar adhesion test apparatus and method for paints and finishes.

Referring now to FIG. 2b, in embodiments, anti-scratch coatings 214 and structures 216 prevent marring of the coating 122 by the flexible scalpel tip 206 and adjustable mechanical guide 212 during testing. In embodiments, the flexible scalpel tip 206 is coated is an anti-scratch coating 214. Example anti-scratch coatings 214 include plastic, polycarbonate, Teflon® or polytetrafluoroethylene coatings, polyurethane or comparable materials. In embodiments, the adjustable mechanical guide 212 comprises plastic, polycarbonate, or other anti-scratch materials, or includes an anti-scratch coating 214. In embodiments, the adjustable mechanical guide 212 further comprises structures 216 that allow the adjustable mechanical guide 212 to glide over the article under test 120 without scratching, for example wheels, rollers, ball bearing, or pads having low coefficients of friction.

Referring now to FIG. 3, an exemplary embodiment of the operation 300 of an ultrasonic adhesion test apparatus 100, 200 is presented. The ultrasonic adhesion test apparatus 100, 200 is calibrated 302 by adjusting the apparatus so that the scalpel tip 106, 206 will apply the intended, calibrated, pressure against the coating 122. The ultrasonic adhesion test apparatus 100, 200 is positioned 304 over the article under test 120. Ultrasound waves at the intended power level are generated 306 in the scalpel tip 106, 206, and the scalpel tip 106, 206 is applied 308 against the coating 122 at a consistent pressure. The scalpel tip 106, 206 of the ultrasonic adhesion test apparatus 100, 200 is then translated, or moved 310 across the coating 122 at a rate of approximately 0.5 inches for approximately 1 inch. The action of the pressure from the scalpel tip 106, 206 moving across the coating 122 in addition to the ultrasonic waves removes 312 any coating 122 that is not adhering properly to the underlying substrate 124, thus indicating a substandard, or insufficient, amount of adhesion of the coating 122 to the substrate 124. Finally, the coating 122 is inspected 314 to determine if any of the coating 122 has been removed, thus exposing the substrate 124. In embodiments, the inspection is performed by the user by visually inspecting the coating 122. Alternatively, the inspection is performed electronically by cameras or specialized vision equipment at the appropriate frequency bands for detection of coatings 122 that have been removed, for example by identifying areas of exposed substrate 124. In embodiments, the inspecting includes analysis of the removed coatings 122 or exposed substrate 124, for example to determine the amount of coating 122 removed, the shape of the affected coating 122, or other distinguishing characteristics indicative of insufficient adhesion of the coating 122 to the substrate 124.

The embodiments of the invention shown in the drawings and described above are exemplary of numerous embodiments that may be made within the scope of the appended claims. It is contemplated that numerous other configurations of the system and method for providing an ultrasonic adhesion test apparatus and method may be created taking advantage of the disclosed approach. It is the applicant's intention that the scope of the patent issuing herefrom will be limited only by the scope of the appended claims.

What is claimed is:

1. An apparatus for testing the adhesion of a coating on an article to a substrate, the apparatus comprising:
   a body;
   a source of ultrasonic waves;
   a flexible scalpel tip extending from said body that receives said ultrasonic waves and is configured to contact and apply a predetermined pressure and said ultrasonic waves to the coating; and
   a source of water for cooling said flexible scalpel tip; and
   wherein said predetermined pressure of said flexible scalpel tip and said ultrasonic waves remove the coating from the substrate when the adhesion of the coating to the substrate is substandard.

2. The apparatus of claim 1, further comprising:
   a mechanical guide in proximity to said flexible scalpel tip, wherein said mechanical guide regulates said predetermined pressure of said flexible scalpel tip against the coating; and
   wherein said mechanical guide is adapted to be pressed against the coating at a second predetermined pressure that maintains contact between said mechanical guide and the coating.

3. The apparatus of claim 2, wherein said mechanical guide is an adjustable mechanical guide for calibrating said predetermined pressure of said flexible scalpel tip against the coating to a calibrated pressure, and wherein said calibrated pressure of said flexible scalpel tip in combination with said ultrasonic waves removes the coating from the substrate when the adhesion of the coating to the substrate is substandard, and wherein said flexible scalpel tip extends through said adjustable mechanical guide and protrudes outside said adjustable mechanical guide.

4. The apparatus of claim 2, said mechanical guide further comprises a means for sliding against the coating without substantially marring the coating.

5. The apparatus of claim 4, wherein said means for sliding is selected from the group consisting of a wheel, a roller, a ball bearing, a pad having low coefficients of friction, a plastic structure, a polycarbonate structure, a polytetrafluoroethylene coating, a polyurethane coating, and an anti-scratch coating.

6. The apparatus of claim 1, further comprising:
   means for detecting said predetermined pressure of said flexible scalpel tip against the coating; and
   means for displaying said detected predetermined pressure.

7. The apparatus of claim 1, wherein said flexible scalpel tip is a metal scalpel further comprising an anti-scratch coating.

8. The apparatus of claim 7, wherein said anti-scratch coating is selected from the group consisting of a plastic coating, a polycarbonate coating, a polytetrafluoroethylene coatings, and a polyurethane coating.

9. The apparatus of claim 1, further comprising:
   an ultrasonic transducer in said body in communication with said flexible scalpel tip;
   an electronic circuit in said body for driving said ultrasonic transducer; and
   a power source for powering said electronic circuit.

10. The apparatus of claim 9, wherein said power source is a battery in said body.

11. The apparatus of claim 9, further comprising:
    means for adjusting a power level of said electronic circuit; and
    means for displaying said power level.

12. A method of testing the adhesion of a coating on an article to a substrate, the method comprising:
    applying an ultrasonic adhesion test device at a predetermined pressure onto the coating, said ultrasonic adhesion test device comprising a flexible scalpel tip extending from said ultrasonic adhesion test device and contacting the coating at said predetermined pressure;
    applying a plurality of ultrasonic waves onto the coating from said flexible scalpel tip;
    moving said ultrasonic adhesion test device across the coating, wherein said flexible scalpel tip, said ultrasonic waves, and said operation of moving remove at least a portion of the coating from the substrate when there is insufficient adhesion of the portion of the coating to the substrate; and
    inspecting the coating for insufficient adhesion of the coating to the substrate.

13. The method of claim 12, further comprising:
    calibrating a power level of said ultrasonic waves to remove said at least a portion of the coating from the substrate when there is insufficient adhesion of said at least a portion of the coating to the substrate.

14. The method of claim 12, wherein said ultrasonic adhesion test device further comprises a mechanical guide in proximity to said flexible scalpel tip, wherein said predetermined pressure maintains contact between said mechanical guide and the coating, and wherein said mechanical guide regulates a scalpel tip pressure applied by said flexible scalpel tip onto the coating, and further comprising applying said flexible scalpel tip at said scalpel tip pressure on the coating.

15. The method of claim 14, further comprising:
    calibrating said mechanical guide such that said scalpel tip pressure in combination with said ultrasonic waves and said operation of moving said ultrasonic adhesion test device across the coating removes the coating from the substrate when the adhesion of said at least a portion of the coating to the substrate is less than an acceptable adhesion.

16. The method of claim 12, wherein said operation of moving said ultrasonic adhesion test device across the coating is performed at a rate of approximately 0.5 inches per second.

17. The method of claim 12, wherein said operation of moving said ultrasonic adhesion test device across the coating is performed for a distance of approximately 1 inch.

18. A system, comprising:
    means for generating a plurality of ultrasonic waves in a scalar tip;
    means for pressing said scalar tip onto a coating on an article at a predetermined, consistent pressure, said scalar tip coupling said ultrasonic waves to said coating;
    means for translating said scalar tip across said coating; and
    means for cooling said scalar tip; and
    wherein said consistent pressure of said scalar tip on said coating, said translating of said scalar tip across said coating, and said coupling of said ultrasonic waves to said coating removes said coating from an underlying substrate when there is insufficient adhesion of said coating to said underlying substrate.

19. The system of claim 18, wherein said means for pressing said scalar tip onto said coating of said manufactured article further comprises an adjustable mechanical guide for calibrating said predetermined, consistent pressure.

20. The system of claim 18, wherein said means for translating said scalar tip across said coating of said article further comprises an adjustable mechanical guide that contacts said coating at a second pressure to maintain contact of the adjustable mechanical guide with said coating, said scalar tip extending through said adjustable mechanical guide and pressing onto said coating at said predetermined, consistent pressure.

* * * * *